(12) United States Patent
Miyata et al.

(10) Patent No.: US 8,814,890 B2
(45) Date of Patent: Aug. 26, 2014

(54) VASCULAR CATHETER

(75) Inventors: Naohiko Miyata, Aichi-ken (JP);
Manabu Shimogami, Aichi-ken (JP);
Masaaki Nihonmatsu, Aichi-ken (JP);
Shinichi Goto, Aichi-ken (JP)

(73) Assignee: Asahi Intecc Co., Ltd., Aichi-Ken (JP)

( * ) Notice: Subject to any disclaimer, the term of this patent is extended or adjusted under 35 U.S.C. 154(b) by 1047 days.

(21) Appl. No.: 11/098,599

(22) Filed: Apr. 5, 2005

(65) Prior Publication Data
US 2005/0222585 A1 Oct. 6, 2005

(30) Foreign Application Priority Data
Apr. 6, 2004 (JP) ................................. 2004-112517

(51) Int. Cl.
*A61B 17/22* (2006.01)
*A61B 17/00* (2006.01)
*A61M 25/00* (2006.01)
*A61B 17/34* (2006.01)

(52) U.S. Cl.
CPC .... *A61M 25/005* (2013.01); *A61B 2017/00292* (2013.01); *A61M 25/0069* (2013.01); *A61B 2017/349* (2013.01); *A61M 25/0068* (2013.01); *A61M 25/0053* (2013.01); *A61M 25/0043* (2013.01); *A61M 25/0082* (2013.01); *A61M 25/0021* (2013.01); *A61B 2017/00685* (2013.01); *A61B 2017/00902* (2013.01)
USPC ...................................................... 606/159

(58) Field of Classification Search
USPC ........... 606/159, 191, 184, 185, 113; 604/525
See application file for complete search history.

(56) References Cited

U.S. PATENT DOCUMENTS

| 3,815,608 | A |   | 6/1974 | Spinosa et al. ............ 128/349 R |
| 4,368,730 | A |   | 1/1983 | Sharrock ....................... 604/158 |
| 4,370,131 | A | * | 1/1983 | Banko ............................. 433/86 |
| 4,748,986 | A | * | 6/1988 | Morrison et al. ............. 600/585 |
| 5,078,723 | A |   | 1/1992 | Dance et al. .................. 606/159 |
| 5,314,438 | A |   | 5/1994 | Shturman ..................... 606/159 |

(Continued)

FOREIGN PATENT DOCUMENTS

| EP | 0 495 299 A1 | 7/1992 |
| JP | 58-095802 U | 6/1983 |

(Continued)

OTHER PUBLICATIONS

EP Search Report for corresponding European Patent Application No. 05252149.9 issued Sep. 5, 2005.

(Continued)

*Primary Examiner* — Thomas McEvoy
*Assistant Examiner* — Julie A Szpira
(74) *Attorney, Agent, or Firm* — Morgan, Lewis & Bockius LLP

(57) ABSTRACT

In a medical equipment, a hollow shaft body is made of single-wound or plurally-wound coil line elements, and has a cylindrical tip portion formed on a distal end of the hollow shaft body, and a manipulative grip connected to a proximal side portion of the hollow shaft. At least one of an inner surface mid an outer surface of the hollow shaft, and at least one of an inner surface and outer surface of the tip portion are provided with a screw-like concave-convex streak of projection. The hollow shaft body has a diameter-reduced portion at the manipulative grip having a transparent portion, through which the diameter reduced portion is visible from outside.

8 Claims, 4 Drawing Sheets

(56) References Cited

U.S. PATENT DOCUMENTS

| | | | | |
|---|---|---|---|---|
| 5,755,697 | A * | 5/1998 | Jones et al. | 604/174 |
| 5,891,055 | A | 4/1999 | Sauter | 600/585 |
| 6,059,807 | A * | 5/2000 | Boudjema | 606/187 |
| 6,106,538 | A * | 8/2000 | Shiber | 606/184 |
| 6,139,557 | A * | 10/2000 | Passafaro et al. | 606/159 |
| 6,638,265 | B1 * | 10/2003 | Ternamian | 604/523 |
| 7,153,319 | B1 * | 12/2006 | Haberland et al. | 606/185 |
| 2002/0045855 | A1 | 4/2002 | Frassica | 604/109 |
| 2002/0077686 | A1 * | 6/2002 | Westlund et al. | 607/119 |
| 2003/0195467 | A1 * | 10/2003 | Mickley | 604/117 |
| 2003/0216761 | A1 | 11/2003 | Shiber | 606/159 |
| 2004/0243108 | A1 * | 12/2004 | Suzuki | 606/1 |
| 2004/0249277 | A1 * | 12/2004 | Kato et al. | 600/434 |
| 2007/0083220 | A1 * | 4/2007 | Shamay | 606/159 |
| 2007/0282358 | A1 * | 12/2007 | Remiszewski et al. | 606/159 |
| 2008/0140104 | A1 * | 6/2008 | Bender et al. | 606/170 |
| 2008/0154294 | A1 * | 6/2008 | Semm | 606/185 |

FOREIGN PATENT DOCUMENTS

| | | |
|---|---|---|
| JP | 59-16649 U | 2/1984 |
| JP | 59-184809 U | 12/1984 |
| JP | 60-261465 | 12/1985 |
| JP | 63-262160 | 10/1988 |
| JP | 06-047094 | 2/1994 |
| JP | 07-265315 | 10/1995 |
| JP | 07-265319 | 10/1995 |
| JP | 09-094297 | 4/1997 |
| JP | 09-094298 A | 4/1997 |
| JP | 10-165361 A | 6/1998 |
| JP | 11-089941 A | 4/1999 |
| JP | 2000/161543 | 6/2000 |
| JP | 2001-327606 A | 11/2001 |
| JP | 2002-532164 | 10/2002 |
| JP | 2002/539901 | 11/2002 |
| JP | 2003-520651 A | 7/2003 |
| JP | 2004-501672 | 1/2004 |
| JP | P2004-509659 A | 4/2004 |
| JP | 2004-533271 A | 11/2004 |
| WO | WO 00/35527 | 6/2000 |
| WO | 00-57944 | 10/2000 |
| WO | WO 01/51114 | 7/2001 |
| WO | WO 01/54761 A2 | 8/2001 |
| WO | WO 01/91653 | 12/2001 |
| WO | WO 02/28467 | 4/2002 |

OTHER PUBLICATIONS

Office Action issued for the corresponding European Patent Application No. 05252149.9 dated Mar. 17, 2006.
Office Action issued for the corresponding European Patent Application No. 05252149 dated Apr. 22, 2008.
First Office Action issued for the corresponding Chinese Patent Application No. 200510071630.9 dated Mar. 7, 2008.
Second Office Action issued for the corresponding Chinese Patent Application No. 200510071630.9 dated Aug. 29, 2008.
Third Office Action issued for the corresponding Chinese Patent Application No. 200510071630.9 dated Dec. 12, 2008.
Submission of Information submitted for the corresponding Japanese Patent Application No. 2004-112517 dated Jan. 17, 2006.
Akira Negishi "About Shape Memory Alloys," Chapter 5: Applications of Shape Memory Alloy (Superelastic Alloy), Masaki Seike, Japanese Standards Association, Oct. 16, 1989.
Notification of Reasons for Rejection (Office Action) issued for the corresponding Japanese Patent Patent Application No. 2004-112517 dated Dec. 8, 2009.
Notification of Reasons for Rejection (Office Action) issued for the corresponding Japanese Patent No. 2004-112517 dated Feb. 26, 2010.
Notification of Reasons for Rejection (Office Action) issued for the corresponding Japanese Patent Application No. 2010-065485 dated Sep. 13, 2010.
Notification of Reasons for Rejection (Office Action) issued for the corresponding Japanese Patent Application No. 2010-065485 dated Dec. 14, 2010.

* cited by examiner

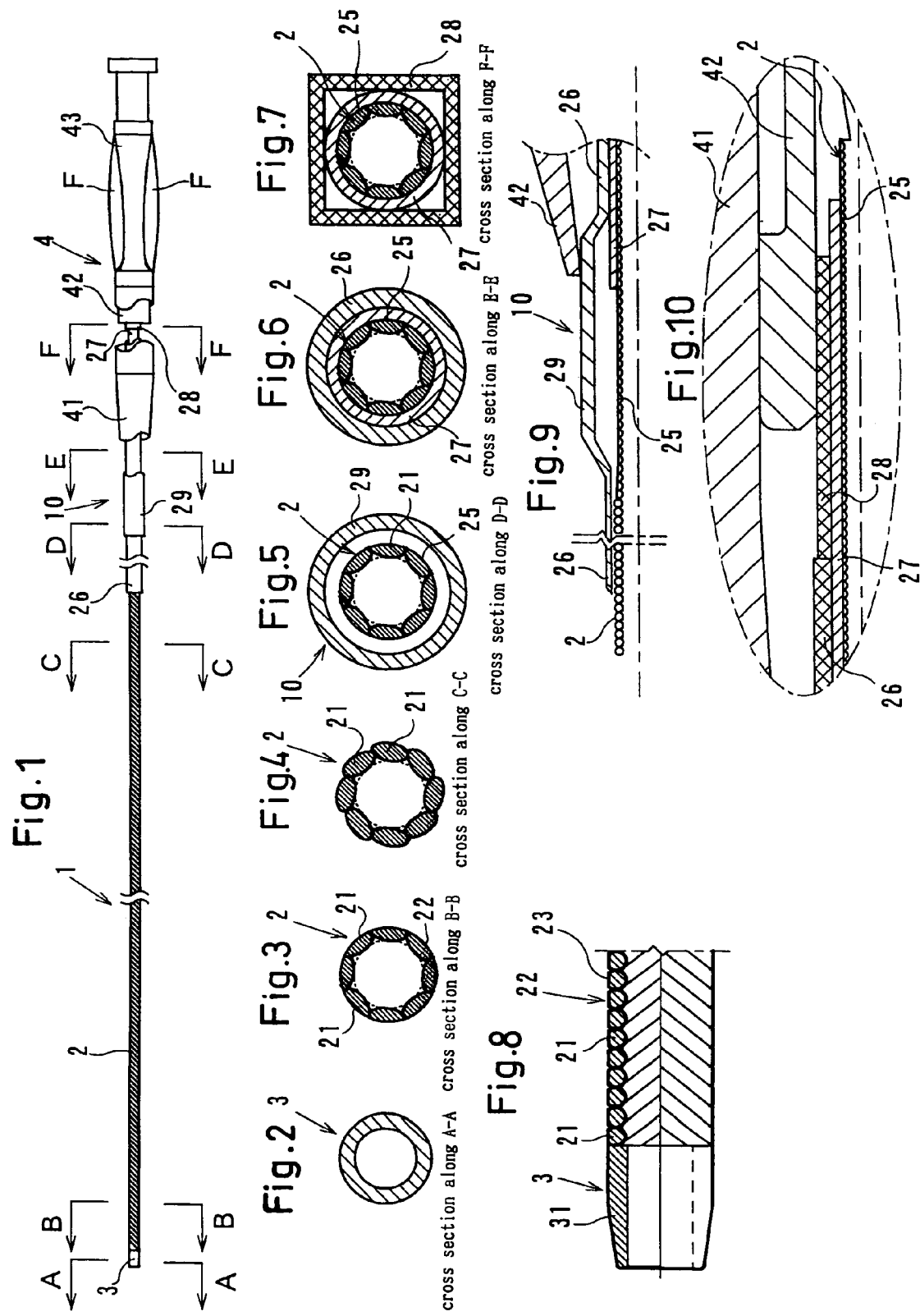

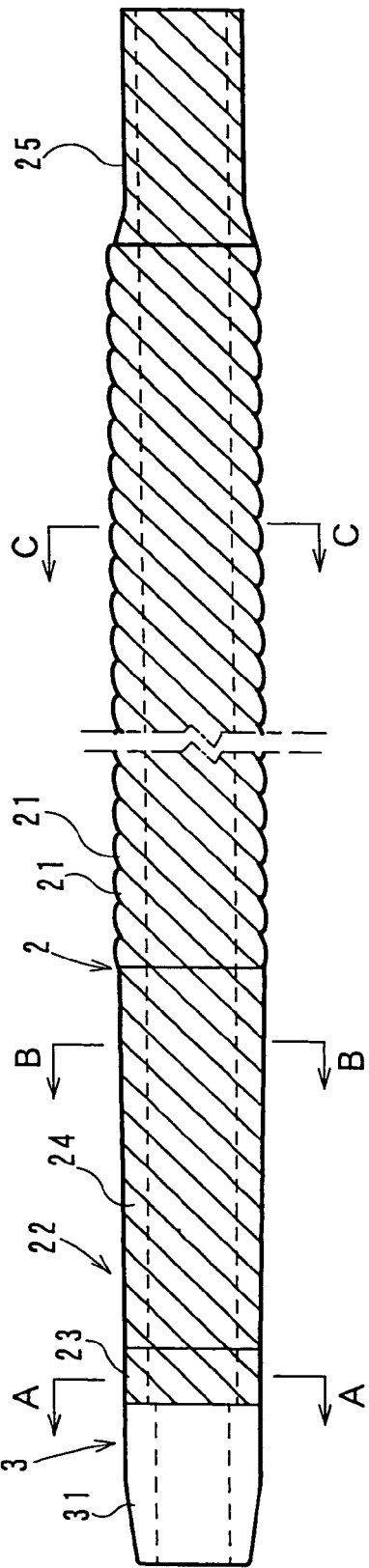
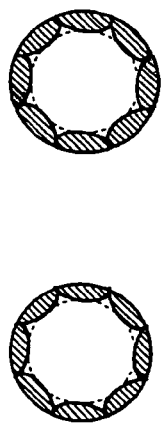
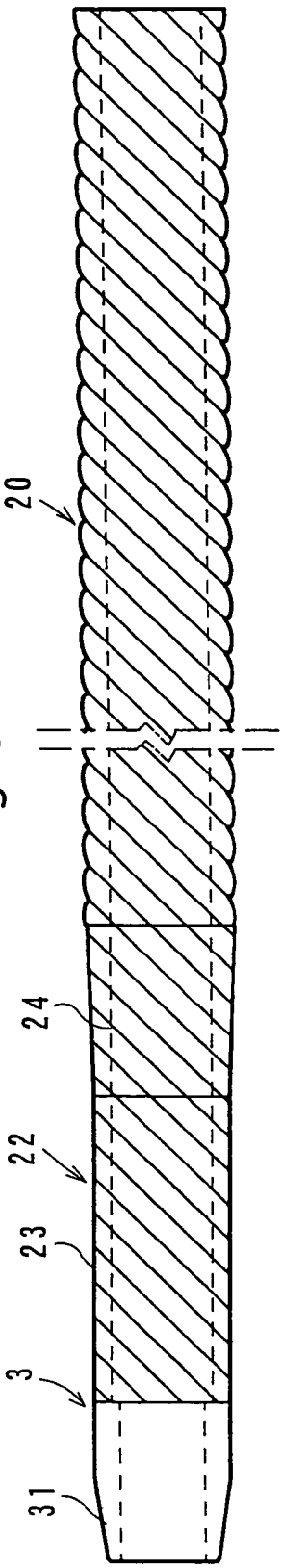

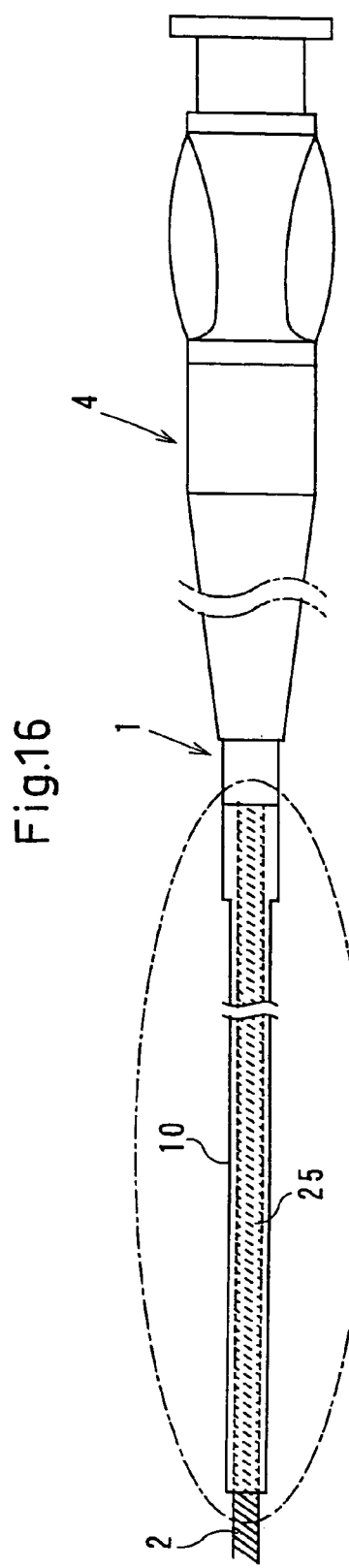
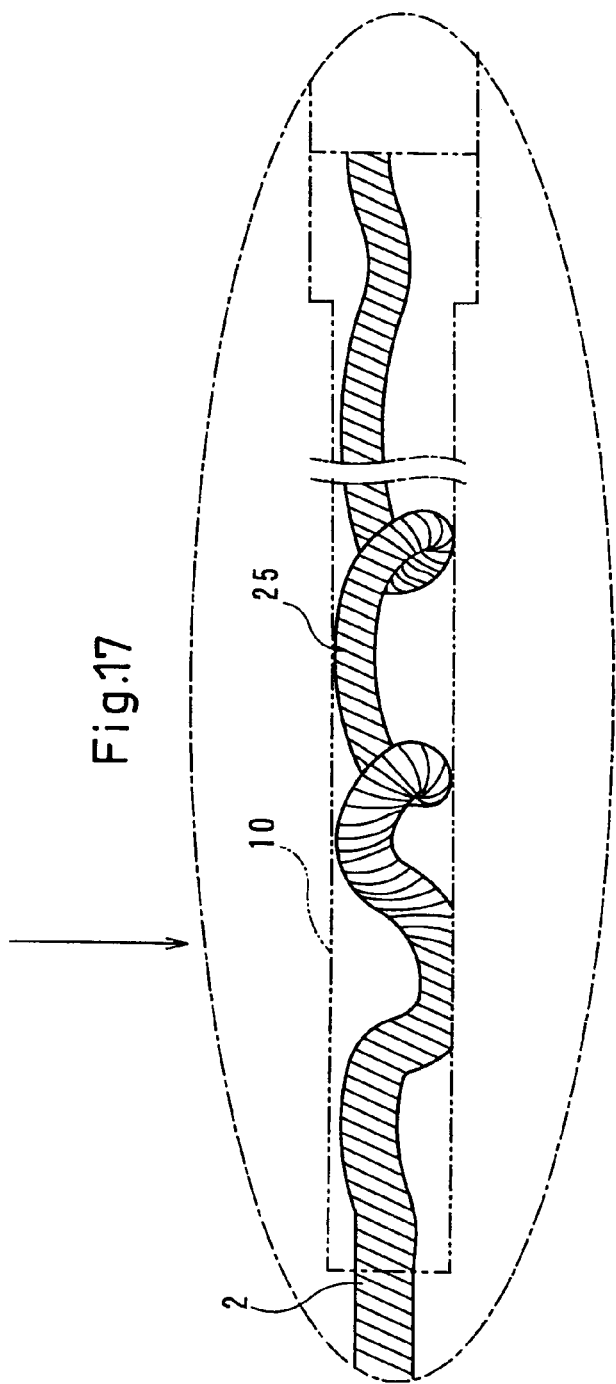

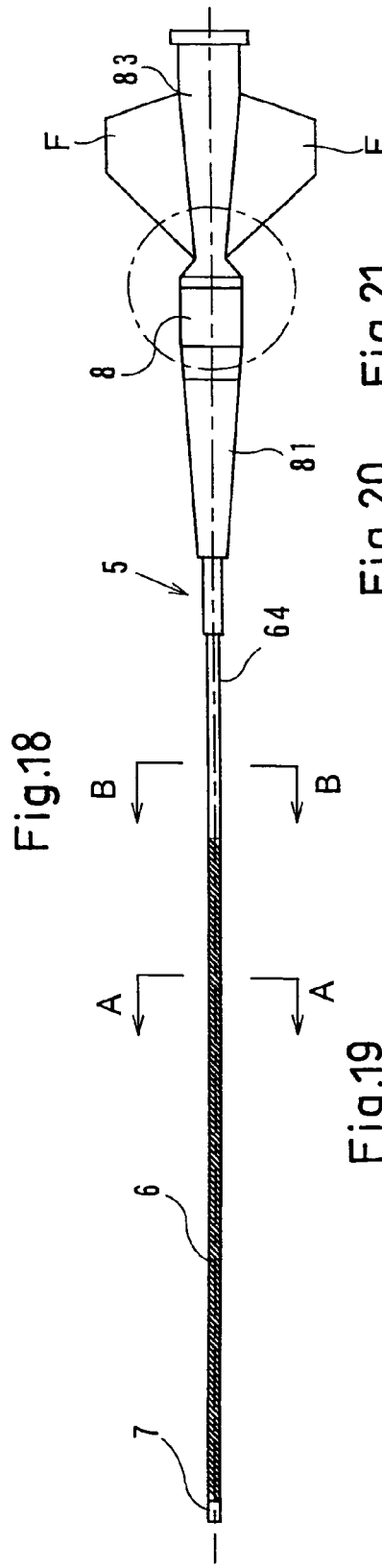
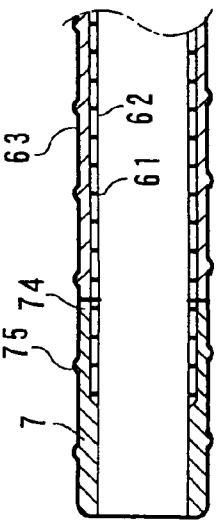
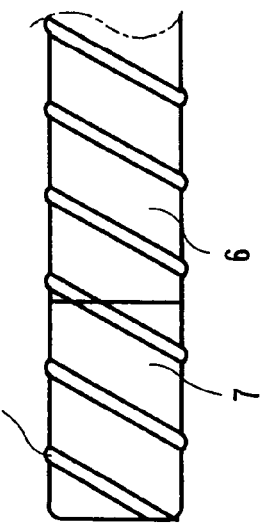
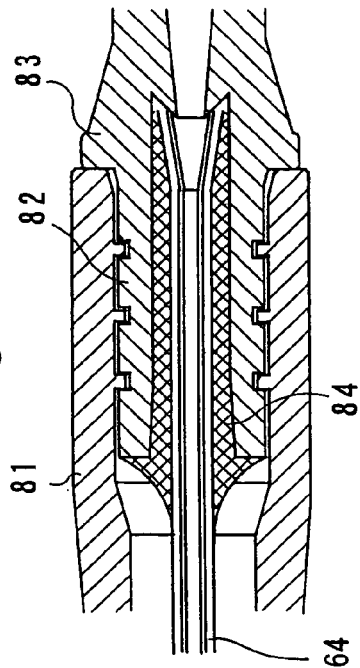

VASCULAR CATHETER

BACKGROUND OF THE INVENTION

1. Field of the Invention

The invention relates to a medical equipment used for a penetration or a dilatation against an occlusive area and a stenotic area in a blood vessel.

2. Description of Related Art

A dilatation catheter, a micro catheter (very thin in outer diameter) and an atherectomy catheter with an ablative tool have been used for a penetration and a dilatation against the occlusive area and the stenotic area in the blood vessel as shown by Japanese Laid-open Patent Application No. 7-265319.

The dilatation catheter and the micro catheter are crossed into the blood vessel by a pushing force with the assist of a guide catheter. When the occlusive area and the stenotic area are stiffened, only the guide catheter can disengage these areas upon forcibly pushing them against the diseased area.

This makes it difficult for the related art catheters to create the penetration and the dilation against the diseased area. For the atherectomy catheter, although it is appropriate to use for the hard and calcified area, it is ineffective for the atherectomy catheter to cross into the soft vascular tissue.

Therefore, it is an object of the invention to overcome the above drawbacks, and provide a high quality medical equipment which is capable of positively create a penetration against a diseased area which resists a dilatation device to cross over after guide wire has crossed through.

SUMMARY OF THE INVENTION

According to the invention, there is provided a medical equipment having a hollow shaft body, a cylindrical tip portion provided on a distal end of the hollow shaft body, and a grip portion connected to a proximal side portion of the hollow shaft. At least one of an inner surface and an outer surface of the hollow shaft, and at least one of an inner surface and an outer surface of the tip portion are provided with a screw-like concave-convex streak of projection.

The structure is such that the tip portion makes it possible to positively create a penetration against a diseased area which resists a dilatation device to cross through after guide wire has crossed through. This also enables a manipulator to torsionally push the tip portion into the occlusive area in the blood vessel with a smooth maneuverability.

According to the other aspect of the invention, the cylindrical tip portion is made of a radiopaque material, and is welded to the hollow shaft body.

According to the other aspect of the invention, the screw-like concave-convex streak of projection is defined along a plurality of helical winds, a lead length of which is greater than an outer diameter of the hollow shaft body.

According to the other aspect of the invention, a proximal side portion of the hollow shaft body has a portion smaller in yield strength than any parts of the hollow shaft body.

According to the other aspect of the invention, a proximal side portion of the hollow shaft body has a diameter-reduced portion diametrically or cross sectionally smaller than or equal to any parts of the hollow shaft body.

According to the other aspect of the invention, a manipulative grip portion of the hollow shaft body has a transparent portion which makes visible the diameter-reduced portion or a proximal side portion provided on the hollow shaft body to be smaller in yield strength than any parts of the hollow shaft body.

BRIEF DESCRIPTION OF THE DRAWINGS

Preferred forms of the present invention are illustrated in the accompanying drawings in which:

FIG. 1 is a plan view of a medical equipment according to a first embodiment of the invention;

FIG. 2 is a latitudinal cross sectional view taken along the line A-A of FIG. 1;

FIG. 3 is a latitudinal cross sectional view taken along the line B-B of FIG. 1;

FIG. 4 is a latitudinal cross sectional view taken along the line C-C of FIG. 1;

FIG. 5 is a latitudinal cross sectional view taken along the line D-D of FIG. 1;

FIG. 6 is a latitudinal cross sectional view taken along the line E-E of FIG. 1;

FIG. 7 is a latitudinal cross sectional view taken along the line F-F of FIG. 1;

FIG. 8 is a longitudinal cross sectional view of a cylindrical tip portion;

FIG. 9 is a longitudinal cross sectional view of a main portion of the medical equipment;

FIG. 10 is an enlarged cross sectional view of the main portion of the medical equipment;

FIG. 11 is a plan view of a hollow shaft body;

FIG. 12 is a latitudinal cross sectional view taken along the line A-A of FIG. 11;

FIG. 13 is a latitudinal cross sectional view taken along the line B-B of FIG. 11;

FIG. 14 is a latitudinal cross sectional view taken along the line C-C of FIG. 11;

FIG. 15 is a plan view of a modified medical equipment;

FIG. 16 is a plan view of the medical equipment;

FIG. 17 is an enlarged plan view of a main portion of the medical equipment;

FIG. 18 is a plan view of a medical equipment according to a second embodiment of the invention;

FIG. 19 is a longitudinal cross sectional view of a main portion of the medical equipment;

FIG. 20 is a latitudinal cross sectional view taken along the line A-A of FIG. 18;

FIG. 21 is a latitudinal cross sectional view taken along the line B-B of FIG. 18;

FIG. 22 is an enlarged side elevational view of the main portion of the medical equipment;

FIG. 23 is an enlarged cross sectional view of a main portion of the medical equipment.

DETAILED DESCRIPTION OF THE PREFERRED EMBODIMENTS

In the following description of the depicted embodiments, the same reference numerals are used for features of the same type.

Referring to FIGS. 1 through 17 (except FIG. 15), a medical equipment 1 is provided according to a first embodiment of the invention is described below.

As shown in FIGS. 1 through 7, the medical equipment 1 has a hollow shaft body 2 made of a single-wound or plurally wound line coil elements 21 to provide a high flexibility with the hollow shaft body 2. A cylindrical tip portion 3 is welded in one piece to a distal end of the hollow shaft body 2, while a manipulative grip 4 is connected to a proximal side portion of the hollow shaft body 2.

By way of illustration, the tip portion 3 is made of a radiopaque material to serve as a marker when using the medical equipment 1 displayed on an image monitor (not shown).

As show in FIGS. 11 through 14, the hollow shaft body 2 has eight coil line elements 21 made of a stainless steel metal. The coil line elements 21 are helically wound with its lead length, outer diameter and length dimension in turn as 1.2 mm, 0.70 mm and approx. 1350 mm.

A distal end portion of the hollow shaft body 2 has a diameter-reduced portion 22 at the distal end side defined by grinding an outer surface of the hollow shaft body 2. The diameter-reduced portion 22 has measures 0.62 mm in outer diameter, and having a straight portion 23 (10 mm in length) and a tapered portion 24 (150 mm in length). As a modification form, the hollow shaft body 20 has the straight portion 23 (80 mm in length) and the tapered portion 24 (50 mm in length).

It is effective that the hollow shaft body 2 is progressively decreased at its cross sectional area continuously or discontinuously as approaching its distal end portion. It is favorable that the metallic material used for the coil line elements 21 has a tensile strength of more than 120 kgf/mm$^2$ to insure a torque transmissibility. A bulge portion may be formed in a middle of the hollow shaft body 2. A convex-concave screw-like streak of projection may be defined on an outer surface of a cylindrical pipe (stainless steel tube). The coil line elements 21 may be made of a Ni—Ti based alloy.

A proximal rear portion of the hollow shaft body 2 has a diameter-reduced portion 25 at a rear side to be 0.62 mm in outer diameter and 85 mm in length as shown in FIGS. 5-7. An outer diameter of the diameter-reduced portion 25 at the rear side is determined to be smaller than that of the diameter-reduced portion 22 at the distal end side.

This is because a torsional buckling is preferentially induced on the diameter-reduced portion 25 at the proximal rear side. Upon achieving a good screwing efficiency, it is advantageous that the lead length of the coil line elements 21 is greater than the outer diameter of the tip portion 3. The hollow shaft body 2 may be made of a single coil wire tightly would with no gap appeared between its coil line elements.

The tip portion 3 is in the form of a cylindrical platinum metal, and measures 0.62 mm in outer diameter and approx. 1.0 mm in length. An outer surface of the tip portion 3 inclines at a degree of 1/10 to have a tapered portion 31 to works as an ablative tool (gimlet) against the occlusive area and the stenotic area in the blood vessel.

It is necessary for the tapered portion 31 to have a length more than half the entire length of the tip portion 3, and inclining at the rate of 1/5-1/12 inclusive. A concave-convex screw-like streak of projection may be provided with an inner surface or an outer surface of the tip portion 3. A lead length of the screw-like streak of projection is preferably greater than the outer diameter of the tip portion 3 in achieving a good screwing efficiency.

As shown in FIGS. 6 and 9, the hollow shaft body 2 has a tube 26 (350 mm in length) coated along its axial direction extending from the proximal side portion to the diameter-reduced portion 25. A circular protector pipe 27 is firmly interfit into a rear section of the diameter-reduced portion 25. An angular pipe 28 is interfit into the protector pipe 27 at the proximal side portion as shown in FIGS. 6, 7, 9 and 10.

In the proximity of a distal end of the tube 26 in which a distal end of the diameter-reduced portion 25 resides as shown in FIG. 9, a diametrically bulged cylinder 29 is placed in one piece to form a transparent portion 10 so as to render the diameter-reduced portion 25 visible through the transparent portion 10. It is to be noted that the tube 26 may be notched to formed a window section in which a transparent tube is placed to define the transparent portion 10 on the tube 26. The diameter-reduced portion 25 is visible through the transparent portion 10 with a clearance left to permit for the torsional buckling inside the bulged cylinder 29.

As shown in FIGS. 1 and 10, the manipulative grip 4 has a protector cylinder 41 and a cylindrical connector 43 in which a diameter-reduced cylinder 42 is interfit into a proximal rear end of the protector cylinder 41. An outer surface of the connector 43 has diametrically opposed fins F. The diameter-reduced cylinder 42 is interfit into an outer surface of the angular pipe 28 so that the manipulative grip 4 rotationally moves in unison with the rear portion of the hollow shaft body 2.

Upon navigating the medical equipment 1 in the blood vessel to ablate a diseased area (e.g., an occlusive area), the manipulative grip portion 4 controls the tip portion 3 to encounter the occlusive area in the coronary artery, and moving in such a way to provide pushing and torsional force with the hollow shaft body 2.

The hollow shaft body 2, thus provided with the rotational force, exhibits a good screwing effect at contact points against the diseased area, the blood vessel or the guide device. Depending on the rotational direction of the manipulative grip 4, it is possible to screw the tip portion 3 of the medical equipment 1 into the diseased area, while at the same time, withdrawing the tip portion 3 from the diseased area.

Even with no assist of the guide catheter, the manipulative grip 4 makes it possible to cross through the diseased area without forcing the manipulative grip 4 so as to permit penetration and a dilatation for the diseased area under the influence of the Dotter's effect.

The hollow shaft body 2 insures a favorable screwing effect with the increase of the helical pitch length, while the hollow shaft body 2 requires an appropriate tensile-resistant property for the coil line elements 21 to insure a good torque-transmissibility.

As the hollow shaft body 2 increases the flexibility, it becomes easy for the hollow shaft body 2 to follow the curved portion of the blood vessel. When the flexibility extends over the manipulative grip 4, the flexibility decreases the torque-transmissibility for the hollow shaft body 2. In order to avoid this situation, the diameter-reduced portion 22 is provided with the distal end side of the hollow shaft body 2 to progressively decrease its cross sectional area as shown in FIGS. 3 and 8.

The diameter-reduced portion 22 has a length (160 mm) corresponding to the area which reaches the curved portion when inserted into the curved portion of the blood vessel. This insures the flexibility for the distal end portion of the hollow shaft body 2, while at the same time, increasing the torque-transmissibility for the manipulative grip 4.

It is favorable that the diameter-reduced portion 22 extends from 100 mm to 300 mm in length. Under the presence of straight portion 23, it is possible to facilitate the penetration of the diameter-reduced portion 22 into the diseased area.

Due to the tip portion 3 welded in one piece with the hollow shaft body 2, it is possible to insure the physical dimensions and characteristics for the hollow shaft body 2.

Due to the tip portion 3 which has the hollow structure and tapered portion 31 (inclined at the rate of 1/10), it is possible to positively insert the tip portion 3 into the occlusive tissue area in the blood vessel.

During this process, a part of the occlusive tissue invades inside the tip portion 3 to enable the manipulator to smoothly penetrate the occlusive tissue area. With a bulged portion provided on the tip portion 3, it is possible to increase the Dotter's effect to favorably dilate the occlusive tissue area after crossing over through the occlusive tissue area.

When the occlusive tissue area is stiffened, it may happen that the hollow shaft body 2 has the coil line elements 21 gotten loose or torsionally buckled.

In a hollow shaft body 20 devoid of the diameter-reduced portion 25 as a modification form of the invention as shown in FIG. 15, the torsional buckling likely occurs at the diameter-reduced portion 22 of the distal end side such as the straight portion 23 or the tapered portion 24. When the torsional buckling occurs, it would be troublesome to withdraw the medical equipment 1 so as to put the safety at risk.

As shown in FIGS. 16 and 17, the hollow shaft body 2 gets the diameter-reduced portion 25 preferentially buckled to prevent the distal end portion from being buckled inside the blood vessel so as to insure the safety. The transparent portion 10 makes it possible to get the manipulator visually recognize the torsional buckling happen so as to prevent the manipulator from gotten hurt due to fractions of the buckled hollow shaft body 2.

FIGS. 18 through 23 show a second embodiment of the invention in which a medical equipment 5 has a tip portion 7 at a distal section of a hollow shaft body 6 while having a manipulative grip 8 at a proximal section of the hollow shaft body 6.

In this instance, the hollow shaft body 6 has a lower resin layer 62 and an upper resin layer 63. The lower resin layer 62 has a polyamide-based elastomer in which a stainless steel braid work 61 is embedded. The upper resin layer 63 has a polyamide-based elastomer coated over an outer surface of the lower resin layer 62. The hollow shaft body 6 measures 0.70 mm in outer diameter and 0.42 mm in inner diameter. The hollow shaft body 6 has a proximal rear end portion covered by a protector tube 64 to form a flexible elongation structure as a whole.

To the distal end of the hollow shaft body 6, a tip portion 7 is firmly connected which is made of a polyamide-based elastomer. The tip portion 7 has an inner diameter identical to that of the lower resin layer 62, and having an outer diameter identical to that of the upper resin layer 63.

A rear end portion of the tip portion 7 has a thickness-reduced cylinder 74 interfit into an outer surface of a distal end of the lower resin layer 62 as shown in FIG. 19. It is practical to use an adhesive to secure the thickness-reduced cylinder 74 to the distal end of the lower resin layer 62.

At the distal end of outer surface of the tip portion 7 and the hollow shaft body 6, a helical streak of a projection 75 (0.05 mm in height) is formed with its pitch and lead length in turn as 0.5 mm and 1.0 mm.

As shown in FIGS. 18 and 23, the manipulative grip 8 has a tapered protector cylinder 81 and a cylindrical connector 83 in which a diameter-reduced cylinder 82 is interfit into a proximal rear end of the protector cylinder 81. An outer surface of the connector 83 has the diametrically opposed fins F. The diameter-reduced cylinder 82 is interfit into an outer surface of the protector tube 64 through an adhesive layer 84 so that the manipulative grip 8 rotationally moves in unison with the proximal rear portion of the hollow shaft body 6.

In addition to that the medical equipment 5 according to the second embodiment of the invention works in the same way as the first embodiment has acted, the helical streak of the projection 75 enables the manipulator to torsionally push the tip portion 7 into the occlusive area in the blood vessel with a smooth maneuverability.

What is claimed is:
1. A medical equipment comprising:
    a hollow shaft body made of coil line elements helically wound;
    a cylindrical tip portion provided on a distal end of said hollow shaft body;
    a manipulative grip connected to a proximal side portion of said hollow shaft body; and
    a visualization structure disposed on a proximal side of the medical equipment and including a proximal rear portion of said hollow shaft body having a diameter-reduced portion at a rear side the coil line elements of which are half-rounded, said diameter-reduced portion at the rear side being smaller in an outer diameter,
    wherein said visualization structure is configured to be disposed outside of a patient's body and configured to permit a manipulator to visually recognize a torsional buckling of said diameter-reduced portion at the rear side.
2. The medical equipment according to claim 1, wherein a distal end portion of said hollow shaft body has a diameter-reduced portion at a distal end side the coil line elements of which are half-rounded, and an outer diameter of said diameter-reduced portion at the rear side is smaller than that of said diameter-reduced portion at the distal end side.
3. The medical equipment according to claim 1,
    wherein said visualization structure includes a tube coated along an axial direction extending from the proximal side portion of said hollow shaft body to the diameter-reduced portion at the rear side,
    said tube has a transparent portion in which said diameter-reduced portion at the rear side resides, and
    said tube is configured to permit a manipulator to visually recognize said diameter-reduced portion at the rear side through said transparent portion.
4. The medical equipment according to claim 3, wherein said tube has a diametrically bulged cylinder forming said transparent portion to render said diameter-reduced portion at the rear side visible through said transparent portion with a clearance left to permit for the torsional buckling inside said bulged cylinder.
5. The medical equipment according to claim 1, wherein said cylindrical tip portion has a tapered portion on its outer surface to work as an ablative tool against an occlusive area or a stenotic area in a blood vessel.
6. The medical equipment according to claim 1, wherein said diameter-reduced portion at the rear side is defined by grinding an outer surface of said coil line elements.
7. The medical equipment according to claim 1, wherein the cylindrical tip portion has a hollow structure.
8. A medical equipment comprising:
    a hollow shaft body made of coil line elements helically wound;
    a cylindrical tip portion provided on a distal end of said hollow shaft body;
    a manipulative grip connected to a proximal side portion of said hollow shaft body; and
    a proximal rear portion of said hollow shaft body having a diameter-reduced portion at a rear side the coil line elements of which are half-rounded, said diameter-reduced portion at the rear side being smaller in an outer diameter, so that said hollow shaft body gets said diam- eter-reduced portion at the rear side preferentially buckled to get a manipulator to visually recognize a torsional buckling happening, wherein said hollow shaft body has a tube coated along an axial direction extending from the proximal side portion of said hollow shaft body to the diameter-reduced portion at the rear side, said tube has a transparent portion in which said diameter-reduced portion at the rear side resides, so as to visually recognize said diameter-reduced portion at the rear side through said transparent portion, and said tube has a diametrically bulged cylinder forming said transparent portion to render said diameter-reduced portion at the rear side visible through said transparent portion with a clearance left to permit for the torsional buckling inside said bulged cylinder.

\* \* \* \* \*